(12) United States Patent
Williams (10) Patent No.: US 7,647,124 B2
(45) Date of Patent: Jan. 12, 2010

(54) DELIVERY CATHETER

(75) Inventor: Terrell M. Williams, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 11/741,576

(22) Filed: Apr. 27, 2007

(65) Prior Publication Data

US 2007/0203555 A1    Aug. 30, 2007

Related U.S. Application Data

(63) Continuation-in-part of application No. 11/550,715, filed on Oct. 18, 2006, now abandoned, which is a continuation-in-part of application No. 11/273,978, filed on Nov. 15, 2005.

(51) Int. Cl.
*A61N 1/00* (2006.01)
(52) U.S. Cl. .................................................... 607/122
(58) Field of Classification Search .......... 607/115–128
See application file for complete search history.

(56) References Cited

U.S. PATENT DOCUMENTS

| | | | |
|---|---|---|---|
| 4,882,777 A | 11/1989 | Narula | |
| 5,259,395 A | 11/1993 | Li | |
| 5,423,772 A | 6/1995 | Lurie et al. | |
| 5,507,725 A * | 4/1996 | Savage et al. | ............ 604/95.04 |
| 5,542,924 A * | 8/1996 | Snoke et al. | ................. 604/264 |
| 5,683,445 A | 11/1997 | Swoyer et al. | |
| 5,814,028 A * | 9/1998 | Swartz et al. | ................ 604/528 |
| 5,980,505 A * | 11/1999 | Wilson | ........................ 604/525 |
| 6,096,036 A * | 8/2000 | Bowe et al. | .................... 606/41 |
| 6,458,107 B1 | 10/2002 | Ockuly et al. | |
| 2004/0102830 A1 | 5/2004 | Williams | |
| 2004/0122497 A1 | 6/2004 | Zhang et al. | |
| 2004/0147994 A1 | 7/2004 | Zhang et al. | |
| 2005/0070844 A1* | 3/2005 | Chow et al. | ............... 604/95.04 |
| 2005/0137671 A1 | 6/2005 | Liu | |

OTHER PUBLICATIONS

International Search Report, PCT/US2006/060426, Mar. 13, 2007, 5 Pages.

* cited by examiner

*Primary Examiner*—Scott M Getzow
(74) *Attorney, Agent, or Firm*—Carol F. Barry (57) ABSTRACT

A catheter used to deliver a medical electrical lead to a right atrium of a heart in close proximity to a His bundle. The catheter includes a proximal portion and a distal portion.

22 Claims, 7 Drawing Sheets

DELIVERY CATHETER

This application is a continuation-in-part of U.S. patent application Ser. No. 11/550,715 filed on Oct. 18, 2006 which is also a continuation-in-part of U.S. patent application Ser. No. 11/273,978 filed on Nov. 15, 2005.

BACKGROUND OF THE INVENTION

The present invention is related to the delivery of medical electrical leads and more particularly to catheter delivery of such leads to a site in a right atrium of a heart in close proximity to the His bundle.

Various types of medical electrical leads have been developed for endocardial introduction into different chambers of a patient's heart. These flexible leads, various constructions of which are well known in the art, may be delivered using accessory tools, for example a stylet passing through a lumen of a body of the lead, or a catheter having a lumen through which the lead is passed.

A lead implanted in the right atrium can provide pacing therapy to preserve both atrial-ventricular synchronization and the normal ventricular activation and contraction patterns. However, pacing from a right atrial appendage, the typical pacing location in the right atrium, is ineffective if conduction between the right atrium and ventricles is blocked, for example at the AV node of the right atrium. Localized ischemia, inflammation, congenital defects, compression of the AV node, or ablation to prevent conduction as a treatment of atrial fibrillation can be the source of such a block. Ventricular pacing at an apex of the right ventricle is typically employed to bypass such a block, but recent studies have put forth the proposition that problems may arise from pacing at the right ventricular apex because an electrical impulse traveling from the apex moves contrary to the heart's natural conduction pathways. In light of these studies, methods for physiological pacing are currently under investigation; physiological pacing may be defined as stimulation of an intrinsic conduction system of a heart in order to preserve a natural conduction pattern of the heart.

A site of interest for physiological pacing is the His bundle, which is accessible from the right atrium. Existing catheters are not well suited for delivery of an electrical lead to the bundle of His, requiring protracted procedures to reach the desired location. The length of the procedure results in prolonged periods of time in an operating suit causing increased expense and difficulty for the patient as well as greater radiation exposure to the patient. In addition, existing catheters, to the extent they are able to deliver a lead to the His bundle, are generally parallel to the heart surface when they reach the location, making it more difficult to deliver and attach a lead to the underlying cardiac tissue. Thus, there is a need for a tool to facilitate delivery of a medical electrical lead to a site in the right atrium that is in close proximity to the His bundle, for either temporary or permanent pacing stimulation of the His bundle.

SUMMARY OF THE INVENTION

Certain embodiments of the invention include a catheter for delivering and implanting an electrical lead to a right atrium of a heart in close proximity to a His bundle. The catheter includes proximal and distal portions. The distal portion may be hook-shaped, generally planar, and may terminate in a distal tip. The distal portion may also have first and second segments, where the second segment is distal of the first. The second segment curves through an arc of about 100 to 160 degrees to orient the distal tip generally perpendicular to a His bundle when the catheter is implanted. The first segment includes a curvature that springs and orients the second portion towards the His bundle when the catheter is implanted.

Certain embodiments of the invention may include a catheter and lead system for implantation in close proximity to a His bundle. The catheter has a proximal portion and a hook-shaped distal portion that terminates in a distal tip. The distal portion extends over 138 millimeters and through an arc of at least 180 degrees and includes first and second segments. Further, the first and second segments include respective first and second radii of curvature, where the first radius of curvature is greater than the second radius of curvature, which is at least 8 millimeters. The second segment is located distal of the first segment and curves in substantially the same direction as the first segment. The system also includes an electrical lead adapted for implantation via the catheter. The lead has a distal tip electrode that may be implantable to a depth of at least 2 millimeters through the His bundle and secured into the adjacent ventricular myocardium.

BRIEF DESCRIPTION OF THE DRAWINGS

The following drawings are illustrative of particular embodiments of the present invention and therefore do not limit the scope of the invention. The drawings are intended for use in conjunction with the explanations in the following detailed description. Embodiments of the present invention will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention.

Figure 1:
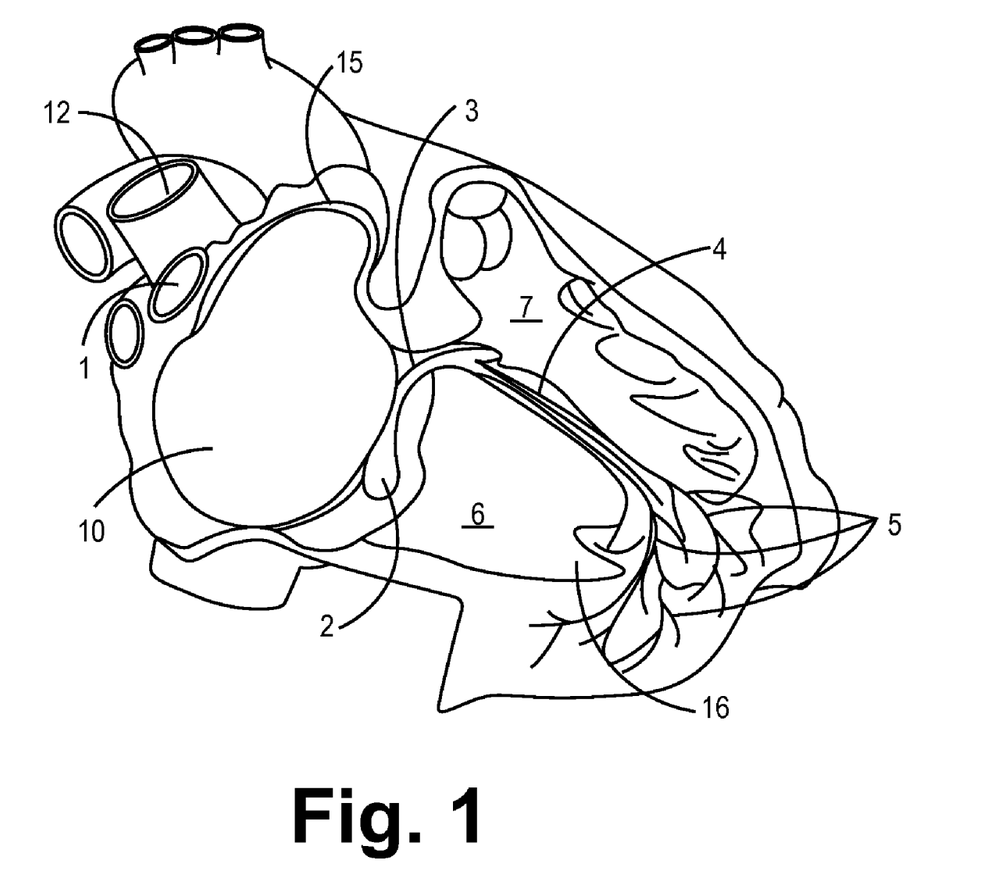
FIG. 1 is a schematic diagram of a right side of a heart having an anterior-lateral wall peeled back.

FIG. 1 is a schematic diagram of a right side of a heart having an anterior-lateral wall peeled back to present a portion of the heart's intrinsic conduction system and chambers of a right atrium (RA) 10 and a right ventricle 6. Pertinent elements of the heart's intrinsic conduction system, illustrated in FIG. 1, include a sinoatrial (SA) node 1, an atrioventricular (AV) node 2, a His bundle 3, a right bundle branch 4, and Purkinje fibers 5. SA node 1 is shown near the superior vena cava (SVC) 12 in the RA 10. An electrical impulse starting at SA node 1 travels rapidly through RA 10 and a left atrium (not shown) and to AV node 2. At AV node 2, the impulse slows to create a delay before passing on through His bundle 3, which branches, in an interventricular septum 7, into a right bundle branch 4 and a left bundle branch (not shown) and then, apically, into Purkinje fibers 5. Flow of the electrical impulse creates an orderly sequence of atrial and ventricular contraction and relaxation to efficiently pump blood through the heart.

When a portion of the heart's intrinsic conduction system becomes damaged, efficient pumping is compromised. A patient, whose SA node 1 has become damaged, may have a pacemaker system implanted wherein lead electrodes are placed in an atrial appendage 15. The lead electrodes stimulate RA 10 downstream of damaged SA node 1 and the stimulating pulse travels on to AV node 2, His bundle 3, and Purkinje fibers 5 to restore physiological contraction of the heart. However, if a patient has a damaged AV node 2, pacing in atrial appendage 15 will not be effective, since the pacing site is upstream of damaged AV node 2. Such a patient may have a pacemaker system implanted wherein lead electrodes are placed in an RV apex 16. RV apex 16 has been an accepted site for pacing since it is a relatively easy to engage lead electrodes at this site, and pacing from this site has been demonstrated safe and effective. Due to questions raised by recent studies looking into long-term effects of pacing from RV apex 16, as previously described, there is a great deal of interest in physiological pacing.

Figure 2:
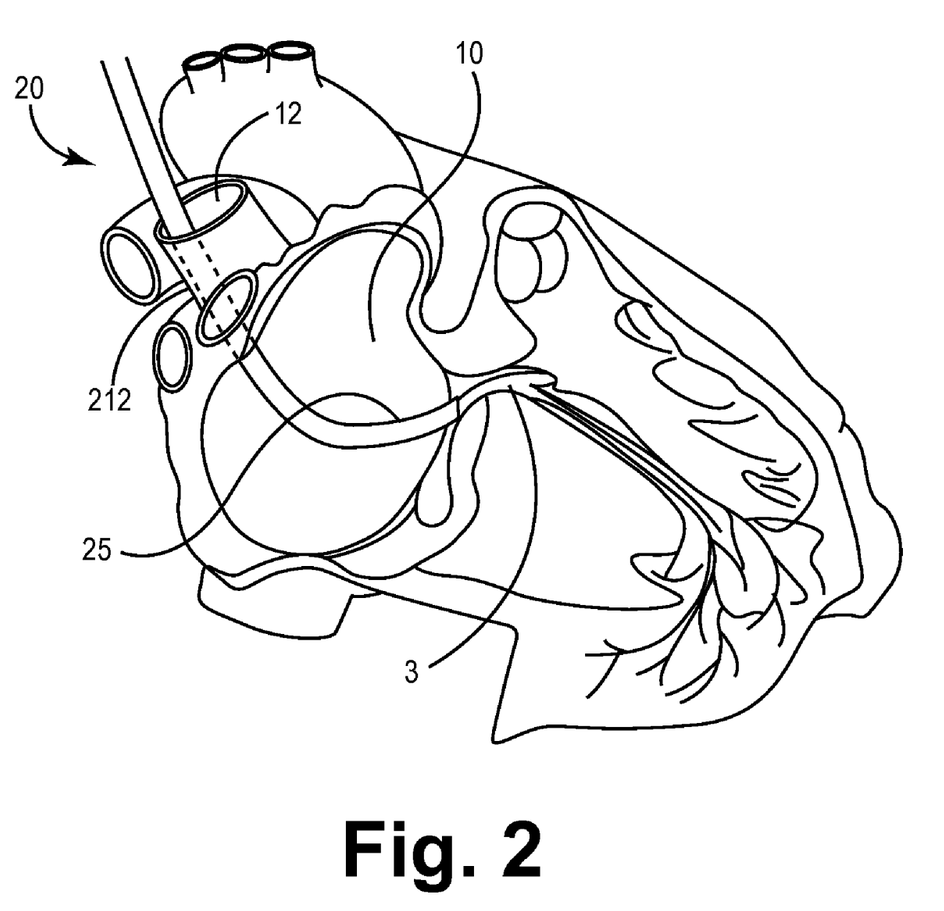
FIG. 2 is a schematic diagram of FIG. 1 in which a distal portion of a delivery catheter, according to some embodiments of the present invention, is positioned.
Figure 3:
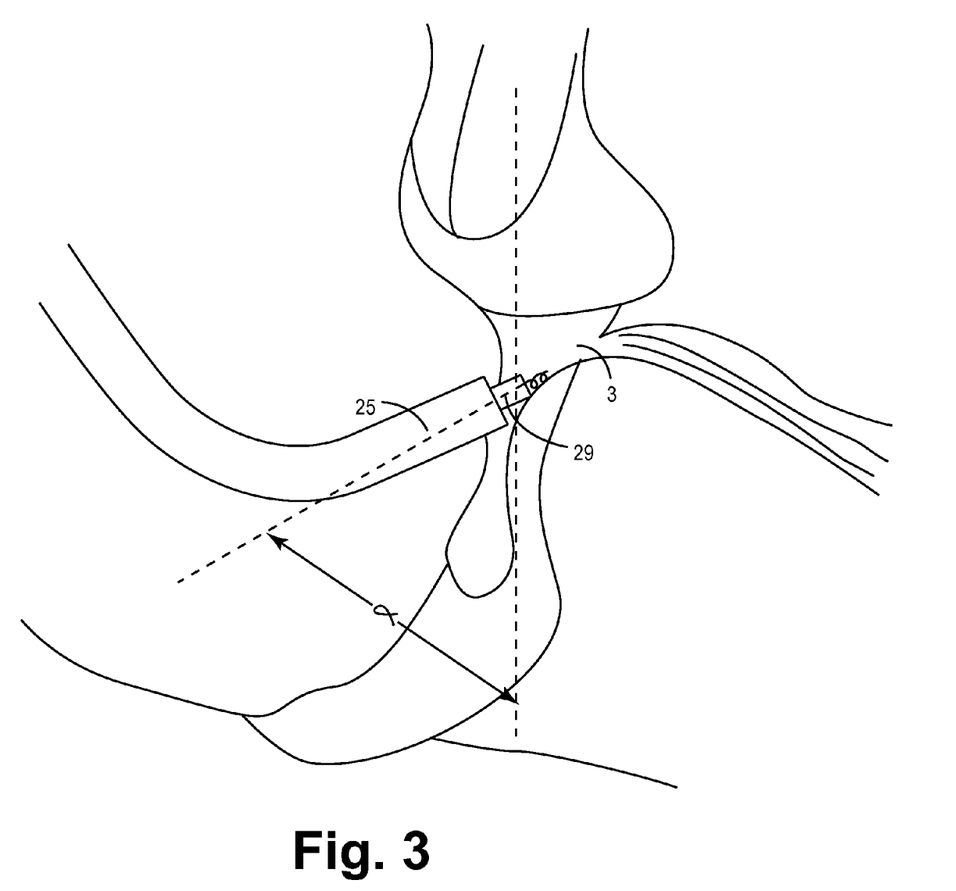
FIG. 3 is an enlarged view of a portion of the schematic diagram of FIG. 1 in which a helical coil and a lead are extending out of a distal portion of a delivery catheter, according to some embodiments of the present invention.

FIG. 2 is the schematic diagram of FIG. 1 in which a distal portion 20 of a delivery catheter, according to some embodiments of the present invention, is positioned. FIG. 2 illustrates delivery catheter distal portion 20 positioned near a junction between SVC 12 and RA 10 so that a distal tip 25 of the catheter is directed toward His bundle 3. In FIG. 3, a medical electrical lead 29 is shown, having been advanced within a lumen of the catheter and extending distally from distal tip 25 to provide physiological pacing. According to one method of the present invention, an operator/physician positions catheter distal portion 20, having passed the catheter into the venous system, for example via a sub-clavian stick, such that a wall 212 of SVC 12 provides back-up support for distal portion 20 as the operator maneuvers tip 25 into a proper orientation and advances lead 29 distally through lumen of the catheter and out tip 25, as shown. Wall 212 of SVC 12 may provide a more stable support for distal portion 20 than a heart wall, for example, not moving as much as a wall of atrium 10 would with each beat of the heart. According to a particular method, catheter distal portion 20 would not contact an atrial wall or a ventricular wall during the positioning and lead delivery processes so as to avoid motion induced by the beating of the heart that may frustrate the operator's effort to accurately place lead 29. Furthermore, it is contemplated that SVC 12 will provide more consistent anatomy for back-up support, from patient to patient, when compared with right atrium 10, so that a large number of variations in distal portion shapes will not be required to track the differences in size of the ventricle.

Certain shapes of curves that are pre-formed in catheter distal portion 20, cooperate with surrounding venous anatomy, for example wall 212 of SVC 12, to assist the operator or physician in positioning catheter distal portion 20 and in delivering lead 29, to a site in close proximity to His bundle 3. Alternate embodiments of catheter distal portion 20, including such pre-formed curves, are presented in FIGS. 4 and 5. It may be seen in FIGS. 4 and 5 that the pre-formed curves extend in a single direction about a generally arc-shaped path such that distal portion 20 is generally hook-shaped. It should be understood that catheter distal portion 20 has a flexibility allowing deformation, depending upon the forces applied when catheter distal portion 20 is being maneuvered within the venous system of a patient, and that configurations or pre-shaped curves of distal portion 20, as illustrated in FIGS. 4 and 5, are in a resting state.

Figure 4:
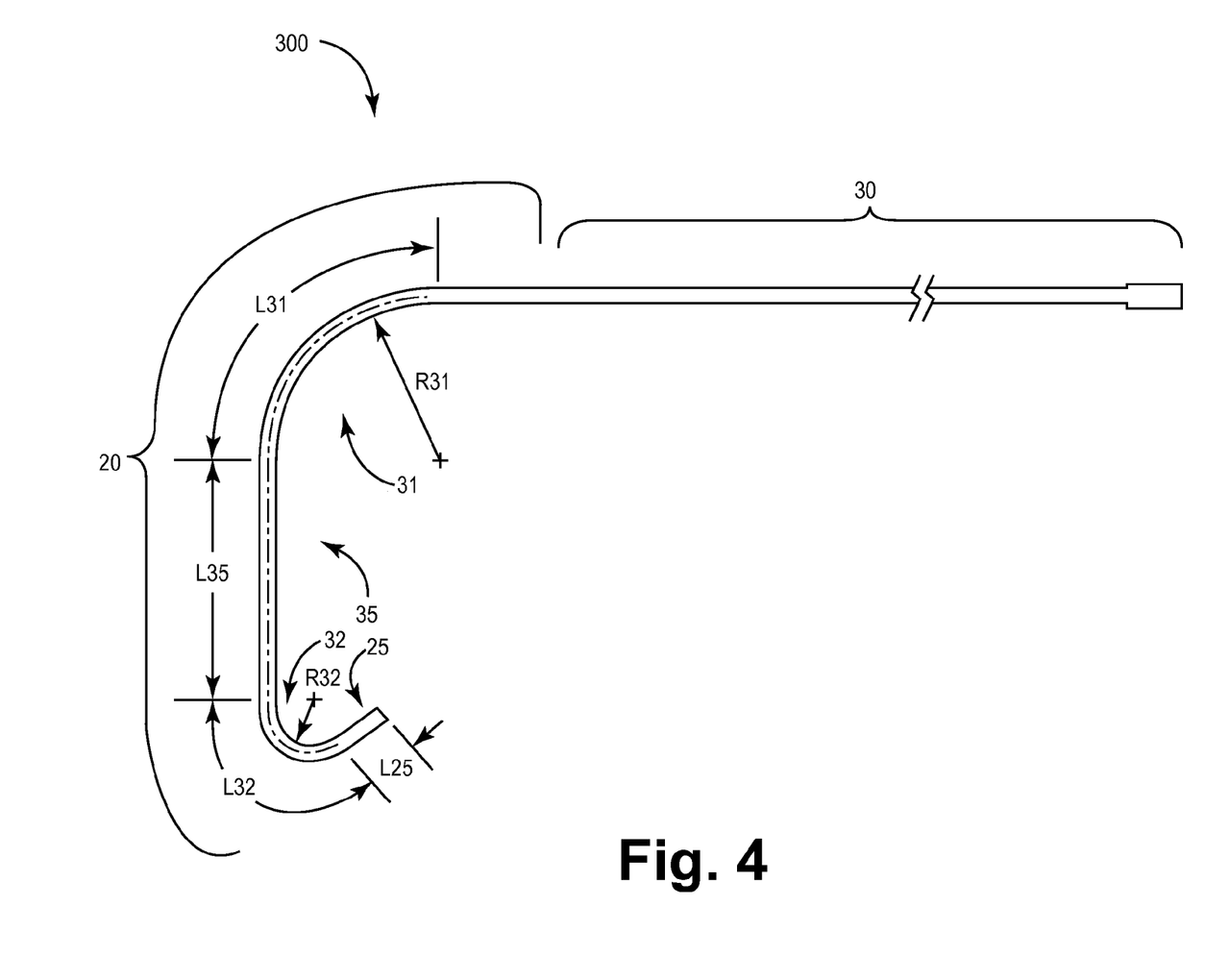
FIG. 4 is plan view of a delivery catheter according to some embodiments of the present invention.
Figure 5:
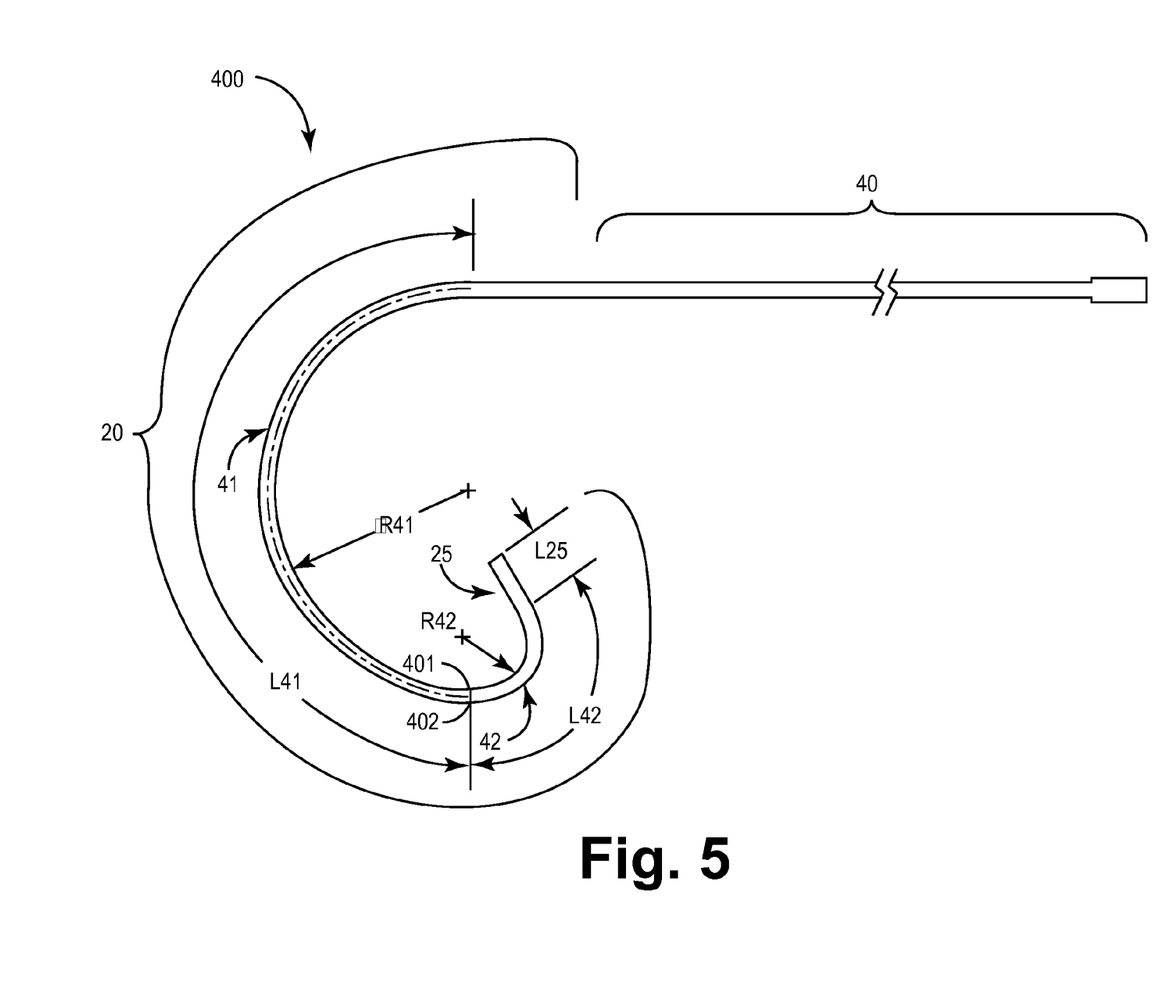
FIG. 5 is a plan view of a delivery catheter according to alternate embodiments of the present invention.

FIG. 4 is plan view of a delivery catheter 300 according to some embodiments of the present invention. FIG. 4 illustrates catheter 300 including a proximal portion 30 and generally hook-shaped distal portion 20 extending from, and coplanar with proximal portion 30. Distal portion 20 includes a first curve 31, a second curve 32, extending distal of first curve 31, and distal tip 25 extending distal of second curve 32. Tip 25 is shown having a length L25, which, according to some embodiments of the present invention, is between approximately 10 millimeters and approximately 12 millimeters, preferably approximately 11 millimeters. According to the illustrated embodiment, a relatively straight or linear intermediate segment 35 is disposed between first curve 31 and second curve 32. According to some embodiments, segment 35 shown in FIG. 4 has a length L35 between approximately 50 millimeters and approximately 60 millimeters, preferably, approximately 53 millimeters.

FIG. 4 further illustrates first curve 31 extending over a length L31 and having a radius R31, and second curve 32 extending over a length L32 and having a radius R32. Tip 25 may be coplanar with the first curve 31 or may be out of plane by as much as approximately 30 degrees. According to some embodiments of the present invention, first curve radius R31 is between approximately 35 millimeters and approximately 45 millimeters, preferably approximately 40 millimeters, and second curve radius R32 is between approximately 8 millimeters and approximately 10 millimeters, preferably approximately 9.5 millimeters. In other embodiments, curves 31 or 32 may not have just one radius. That is, curves 31 or 32 may be more complex and be comprised of several smaller curves having different radii. Length L31 of first curve 31, according to some embodiments, is between approximately 60 millimeters and approximately 70 millimeters, preferably approximately 63 millimeters. Length L32 of second curve 32, according to some embodiments, is between approximately 18 millimeters and approximately 22 millimeters, preferably approximately 20 millimeters. Accordingly, using the length and radius ranges provided above, first curve 31 extends through an arc of about 75 degrees to about 115 degrees. In certain embodiments, first curve 31 only extends through an arc of about 85 degrees to about 100 degrees. Similarly, second curve 32 also then extends through an arc of about 100 degrees to about 160 degrees. In certain embodiments, curve 32 only extends through an arc of about 120 to about 140 degrees.

With respect to the total curvature of curves 31 and 32, in certain embodiments, curves 31, 32 together extend through an arc of about 180 degrees to about 250 degrees. In certain other embodiments, curves 31 and 32 together extend through an arc of about 200 degrees to about 240 degrees.

FIG. 5 is a plan view of a delivery catheter 400 according to alternate embodiments of the present invention. FIG. 5 illustrates catheter 400 including a proximal portion 40 and generally hook-shaped distal portion 20 extending from, and coplanar with, proximal portion 40; distal portion 20 includes a first curve 41, a second curve 42, extending distal to first curve 41, and distal tip 25 extending distal to second curve 42. Tip 25 is shown having a length L25, as in FIG. 4. Tip 25 is shown coplanar with proximal portion 40 and first curve 41, but it may optionally be out of plane by as much as approximately 30 degrees. According to the illustrated embodiment, second curve 42 has a proximal end 402 that is coterminous with a distal end 401 of first curve 41.

FIG. 5 further illustrates first curve 41 extending over a length L41 and having a radius R41, and second curve 42 extending over a length L42 and having a radius R42. According to some embodiments of the present invention, first curve radius R41 is between approximately 30 millimeters and approximately 50 millimeters, preferably approximately 40 millimeters, and second curve radius R42 is between approximately 8 millimeters and approximately 10 millimeters, preferably approximately 9.5 millimeters. In other embodiments, curves 41 or 42 may not have just one radius. That is, curves 31 or 32 may be more complex and be comprised of several smaller curves having different radii. Length L41 of first curve 41, according to some embodiments, is between approximately 120 millimeters and approximately 130 millimeters, preferably approximately 126 millimeters. Length L42 of second curve, according to some embodiments, is between approximately 18 millimeters and approximately 22 millimeters, preferably approximately 20 millimeters. The variation in length may be used to accommodate various heart sizes. Accordingly, using the length and radius ranges provided above, curve 41 extends through an arc of about 135 degrees to about 250 degrees. In certain embodiments, curve 41 only extends through an arc of about 165 degrees to about 205 degrees. Similarly, curve 42 also then extends through an arc of about 100 degrees to about 160 degrees. In certain embodiments, curve 42 only extends through an arc of about 120 to about 140 degrees.

With respect to the total curvature of curves 41 and 42, in certain embodiments, curves 41, 42 together extend through an arc of about 180 degrees to about 340 degrees. In certain other embodiments, curves 41 and 42 together extend through an arc of about 250 degrees to about 310 degrees.

The flexible nature of the catheter allows it to advance through the circulatory system and into the heart, while its pre-shaped curved nature provides for proper lead placement. Because the catheter is flexible, it conforms to the shape of the arterial structures as it passes through them and toward the heart. Upon advancing into the right atrium, the catheter rests against the wall 212 of the SVC 12 as described above. Once entering the atrium, a distal portion of the catheter referred to hereinafter as the orienting portion (e.g., at least L32, L25 in FIG. 4, and at least L42, L25 in FIG. 5) regains its curved shape to orient the catheter in the direction towards the bundle of His 3. As described below, this orienting portion of the catheter is adapted to confront the bundle of His 3 generally perpendicularly, or at least at a 45 degree angle. The curvature of the catheter segment proximal to the orienting portion acts as a spring that pushes the orienting portion toward the bundle of His 3. That is, while the catheter rests on the wall 212 of the SVC 12, the first curve 31, 41 of the catheter acts as a spring such that the catheter reaches from its base on the wall of the SVC 12 across the right atrium and curves toward the crest of the ventricular septum, the location of the bundle of His 3. Thus, according to some embodiments of the invention, such as embodiments in which the first and second curve are coterminous as shown in FIG. 5, whether the catheter must reach a shorter distance across the atrium in a smaller heart, or a longer distance in a larger heart, the design of the first curve brings the catheter to the desired location. This occurs because the proximal portion of the first curve 41 remains in the SVC 12 and conforms to its shape, while the distal portion of the first curve 41 curves across the right atrium, bringing the distal end or orienting portion of the catheter to the area of the bundle of His 3. The variation in heart sizes and shapes among individuals results in different locations of the His bundle 3 relative to the SVC 12. However, the design of the catheter including flexible curves ensures that the catheter tip directly engages with the bundle of His 3. In some embodiments, this occurs despite anatomical variations such that in larger hearts, a greater portion of the first curve enters the atrium, curving further, as it must, to reach the bundle of His 3.

The second curve, 32, 42, is placed in the vicinity of the bundle of His 3 by the shape of the first curve 31, 41. The second curve 32, 42, turns the distal tip 25 of the catheter into a proper orientation relative to the interior surface of the wall of the heart at the location at which the lead will be placed. Thus, as shown in FIGS. 4 and 5, the second curve 32, 42, directs the tip 25 of the catheter against the interior wall of the heart such that it abuts the crest of the ventricular septum in a manner that is from generally perpendicular or normal to the interior surface of the wall of the heart at this location. Depending on anatomical variances, the direction of distal tip 25 may be skewed from normal. Therefore, depending on the plane or reference, the angle between the direction of distal tip 25 (taken centrally through the distal tip 25 portion of the catheter) and the interior surface of the heart wall may be 90°±45°. That is, the angle between the distal tip 25 and the interior surface of the heart wall may vary between 45 degrees and 135 degrees. Referring to FIG. 3, the angle between the direction of distal tip 25 (shown in dotted lines) and the interior surface of the heart wall (shown in dotted lines) is represented as the angle α. Angle α may vary between approximately 45 degrees and approximately 135 degrees, such that there is a cone of acceptable angles.

In certain embodiments, the distal tip 25 of the catheter may contain an electrode that senses when the tip 25 is in contact with the heart wall at bundle of His 3, indicating that the catheter is in a proper location for placement of the lead. This is possible because the bundle of His 3 has an electrical potential waveform, distinct from the surrounding tissue, which is a signature waveform known as the His potential. This signature waveform, which has a frequency of approximately 200 Hz, can be sensed by an electrode in the catheter tip, such as, for example, is used in a mapping catheter.

In certain embodiments, a programmer, such as a modified pacing system analyzer, could be incorporated into the catheter system. However, because such programmers are typically optimized for sensing at a rate of approximately 30 Hz, with slow trace speeds for R-wave and P-wave sensing, the programmer trace speed would have to be modified to adjust for the higher frequency content of the bundle of His 3 potentials.

Once the distal tip of the catheter is in the proper location, the lead 29 is advanced through the catheter and is physically and electrically connected to the heart. This connection may be obtained using a helical coil, as one example, to anchor the lead into the cardiac tissue. The alignment of the catheter tip with the interior surface of the heart, being generally perpendicular to approximately 45 degrees askew, facilitates this connection. Preferably, the connection directly couples the lead 29 to the bundle of His 3. It is also preferable for the connection to also connect the lead 29 with the ventricular myocardium, such as by passing through the bundle of His 3 and into the adjacent ventricular cardiac muscle. A helical coil between approximately 1.5 mm and 3.5 mm in length may be used. However, a relatively longer helical coil of approximately 3.5 mm in length may be preferable, as the increased length may allow for better penetration through the bundle of His 3 and into the myocardium. In some embodiments, the helical coil or other connector may release a bioactive agent, for example, by the elution of a steroid from the coil. The drug released could perform a variety of functions, such as decreasing inflammation. An anti-inflammatory effect could be provided, for example, by a steroid eluting from the coil.

A lead connection that penetrates through the bundle of His and into the myocardium provides several advantages. It provides electrical stimulation of the myocardium around the bundle of His 3, allowing for pacing of the heart through an alternate pathway. Under normal conditions, after placing the lead 29, an electrical stimulus to the bundle of His 3 passes through the left and right bundle branches, down the Perkinje fibers and to the ventricals of the heart. This conduction occurs much more quickly than conduction through myocardium, thus it is the dominant pathway and provides the stimulus for the ventricals to contract. However, this conductive pathway could fail in the future, such as due to damage to a component of the pathway caused by ischemia. Should this occur, the stimulus to the myocardium, provided by the lead and no longer dominated by the normal conductive pathways from the bundle of His, would spread through the cardiac muscles and causes ventricular contraction. Thus the lead would continue to pace the heart using an alternative pathway. In addition to conductive advantages, such placement into the myocardium also provides more secure anchoring for the lead. In addition, if the lead is also used for sensing as well as stimulation, placement into the myocardium provides for better sensing of heart activity than placement into the His bundle 3 alone.

It should be noted that the delivery catheters described herein are constructed according to methods well known to those skilled in the art from well known biocompatible materials, and include basic catheter features, for example, a lumen and one or more radiopaque markers. An overall length of the delivery catheters may be between 30 and 60 centimeters, and an outer diameter of the catheters may be between 6 Fr and 14 Fr (1 Fr=0.013 inch).

For easing movement of the delivery catheter, the delivery catheter includes a plurality of segments that have varying durometers which provides increased flexibility and/or stiffness along the length of the catheter. While the delivery catheters are depicted in FIGS. 6-14 as being substantially straight, skilled artisans appreciate that each delivery catheter includes a hooked or curved distal portion as previously described.

Figure 6:
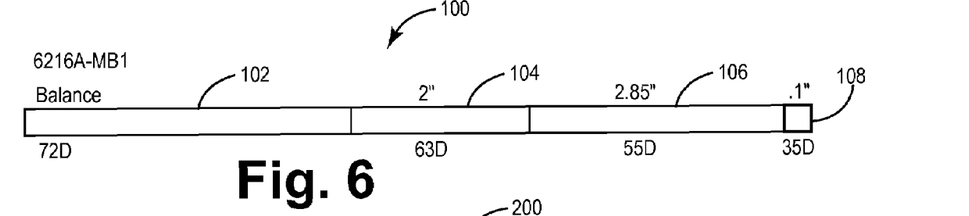
FIG. 6 depicts a top plan view of a delivery catheter with distal segments thereof comprising different durometers.

FIG. 6 discloses a delivery catheter 100 that includes first, second, third and fourth segments 102, 104, 106 and 108. The distal end defined by fourth segment 108 of delivery catheter 100 is about 0.1 inches long and possesses a 35 durometer (D). Third segment 106 is about 2.85 inches long with a durometer of about 55 D. Second segment 104 is about 2.00 inches long with a durometer of about 63 D. First segment 102, which is the proximal end of delivery catheter 100, possesses a durometer of 72 D.

Figure 7:
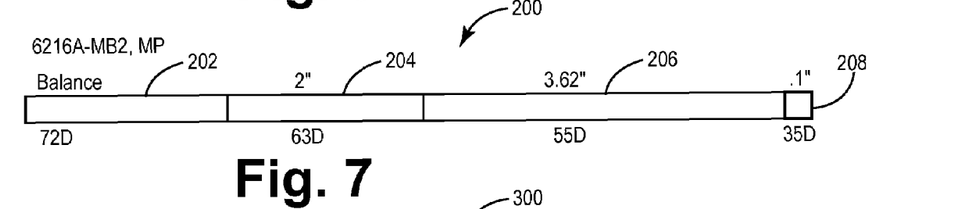
FIG. 7 depicts a top plan view of a delivery catheter with distal segments thereof comprising different durometers.

FIG. 7 depicts a delivery catheter 200 that substantially improves upon conventional catheters. Delivery catheter 200 is defined by first, second, third and fourth segments 202, 204, 206 and 208. Fourth segment 208 is about 0.1 inches long and possesses a 35 D. Third segment 206 is about 3.62 inches long with a durometer of about 55 D. Second segment 204 is about 2.00 inches long with a durometer of about 63 D. First segment 202, which is the proximal end of delivery catheter 200, possesses a durometer of 72 D.

Figure 8:
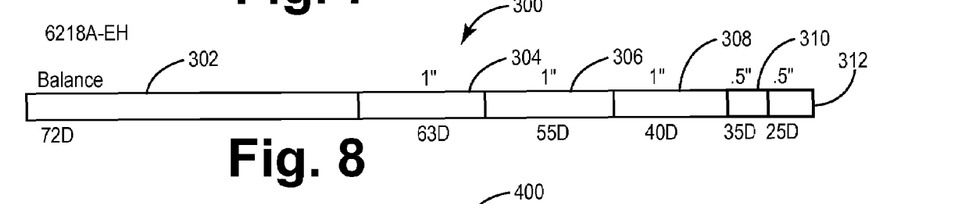
FIG. 8 depicts a top plan view of a delivery catheter with distal segments thereof comprising different durometers.

FIG. 8 discloses a delivery catheter 300. Delivery catheter 300 includes first, second, third, fourth, fifth and sixth segments 302, 304, 306, 308, 310, and 312, respectively. The distal end (sixth segment) 312 of delivery catheter 300 is about 0.5 inches long and possesses a 25 D. The fifth segment 310 is about 0.5 inches long with a durometer of about 35 D. The fourth segment 308 is about 0.5 inches long with a durometer of about 40 D. The third segment 306 is about 1.0 inches long with a durometer of about 55 D. The second segment 304 is about 1.00 inches long with a durometer of about 63 D. The first segment 302, which is the proximal end of delivery catheter 300, possesses a durometer of 72 D.

Figure 9:
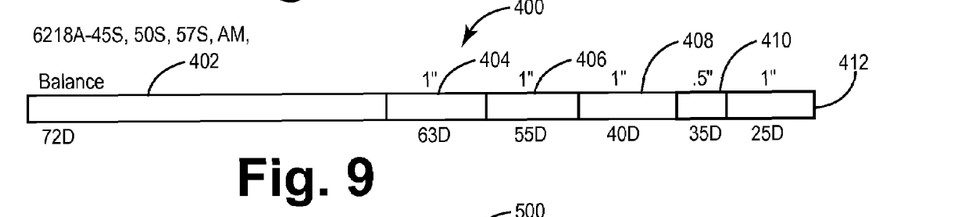
FIG. 9 depicts a top plan view of a delivery catheter with distal segments thereof comprising different durometers.

FIG. 9 discloses a delivery catheter 400. Delivery catheter 400 includes first, second, third, fourth, fifth and sixth segments 402, 404, 406, 408, 410, and 412, respectively. Sixth segment 412 is about 1.0 inches long and possesses a 25 D. Fifth segment 410 is about 0.5 inches long with a durometer of about 35 D. Fourth segment 408 is about 1.0 inches long with a durometer of about 40 D. Third segment 406 is about 1.0 inches long with a durometer of about 55 D. Second segment 404 is about 1.00 inches long with a durometer of about 63 D. First segment 402, which is the proximal end of delivery catheter 400, possesses a durometer of 72 D.

Figure 10:
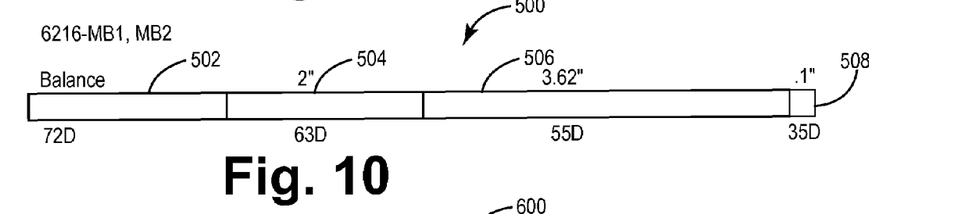
FIG. 10 depicts a top plan view of a delivery catheter with distal segments thereof comprising different durometers.

FIG. 10 discloses an optimal delivery catheter 500. Delivery catheter 500 is defined by first, second, third and fourth segments 502, 504, 506 and 508. The distal end (fourth segment) 508 of delivery catheter 500 is about 0.1 inches long and possesses a 35 D. The third segment 506 is about 3.62 inches long with a durometer of about 55 D. The second segment 504 is about 2.00 inches long with a durometer of about 63 D. The first segment 502, which is the proximal end of delivery catheter 500, possesses a durometer of 72 D.

Figure 11:
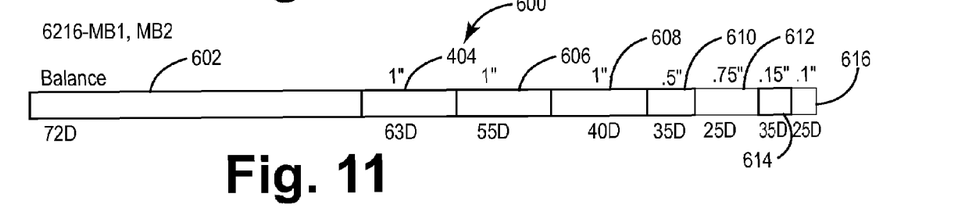
FIG. 11 depicts a top plan view of a delivery catheter with distal segments thereof comprising different durometers.

FIG. 11 discloses a delivery catheter 600. Delivery catheter 600 includes first, second, third, fourth, fifth and sixth, seventh, and eighth segments 602, 604, 606, 608, 610, 612, 614, and 616, respectively. Eighth segment 616 is about 0.1 inches long and possesses a 25 durometer. Seventh segment 612 is about 0.75 inches long with a 25 D material. Sixth segment 612 of delivery catheter 600 is about 0.75 inches long and possesses a 25 D. Fifth segment 610 is about 0.5 inches long with a durometer of about 35 D. Fourth segment 608 is about 1.0 inches long with a durometer of about 40 D. Third segment 606 is about 1.0 inches long with a durometer of about 55 D. Second segment 604 is about 1.00 inches long with a durometer of about 63 D. First segment 602, which is the proximal end of delivery catheter 600, possesses a durometer of 72 D.

Figure 12:
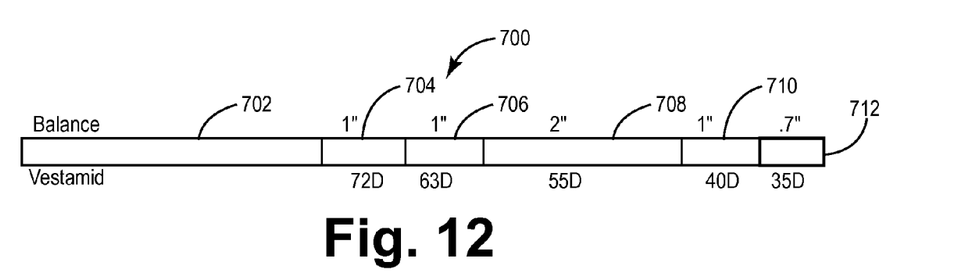
FIG. 12 depicts a top plan view of a delivery catheter with distal segments thereof comprising different durometers.

FIG. 12 discloses a delivery catheter 700. Delivery catheter 700 is defined by first, second, third, fourth, fifth and sixth segments 702, 704, 706, 708, 710, and 712. Sixth segment 712 of delivery catheter 700 is about 0.7 inches long and possesses a 25 D. Fifth segment 710 is about 1.0 inches long with a durometer of about 40 D. Fourth segment 708 is about 2.0 inches long with a durometer of about 55 D. Third segment 706 is about 1.0 inches long with a durometer of about 63 D. Second segment 704 is about 1.00 inches long with a durometer of about 72 D. First segment 702, which is the proximal end of delivery catheter 700, possesses a different durometer.

Figure 13:
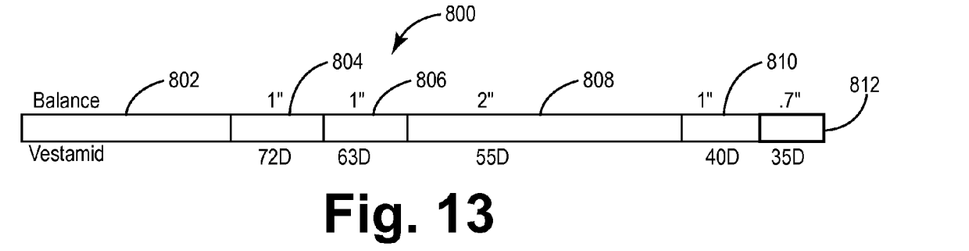
FIG. 13 depicts a top plan view of a delivery catheter with distal segments thereof comprising different durometers.

FIG. 13 discloses a delivery catheter 800. Delivery catheter 800 is defined by first, second, third, fourth, fifth, and sixth segments 802, 804, 806, 808, 810, and 812. Sixth segment 812 of delivery catheter 800 is about 0.7 inches long and possesses a 35 D. Fifth segment 810 of delivery catheter 800 is about 1 inches long and possesses a 40 D. Fourth segment 808 of delivery catheter 800 is about 3 inches long and possesses a 55 D. Third segment 806 is about 1.0 inches long with a durometer of about 63 D. Second segment 804 is about 1.00 inches long with a durometer of about 72 D. First segment 802, which is the proximal end of delivery catheter 800, includes the balance or remaining length of catheter 800.

Figure 14:
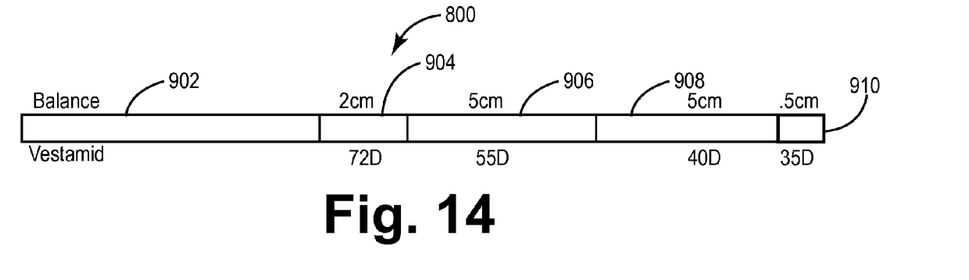
FIG. 14 depicts a top plan view of a delivery catheter with distal segments thereof comprising different durometers.

FIG. 14 discloses a delivery catheter 900. Delivery catheter 900 is defined by first, second, third, fourth, and fifth segments 902, 904, 906, 908, and 910. Fifth segment 910 of delivery catheter 900 is about 0.5 centimeters (cm) long and possesses a 35 D. Fourth segment 908 is about 5 cm long with a durometer of about 40 D. Third segment 906 is about 5.0 cm long with a durometer of about 55 D. Second segment 904 is about 2.0 cm long with a durometer of about 72 D. First segment 902, which is the proximal end of delivery catheter 900, possesses a durometer greater than 72 D.

Ease of moving the delivery catheter into a vein of the patient was established through inserting the delivery catheter into a vein of the patient. A femoral EP mapping/ablation catheter was inserted through a femoral vein and positioned to record a His potential and serve as a fluoroscopic reference. His sensing and pacing was achieved in a short period of time (e.g. 5 minutes and 30 seconds etc.).

In the foregoing detailed description, the invention has been described with reference to specific embodiments. However, it may be appreciated that various modifications and changes can be made without departing from the scope of the invention as set forth in the appended claims.

I claim:

1. A delivery catheter for implanting an electrical lead to a right atrium of a heart in close proximity to a His bundle, the delivery catheter defining a lumen through which an electrical lead can be advanced such that the electrical lead can extend distally from a distal tip terminating the delivery catheter when being implanted, the delivery catheter further comprising:
a proximal portion comprising a first segment of the delivery catheter, wherein the first segment possesses a first durometer (D); and
a distal portion of the delivery catheter being hook-shaped and terminating in the distal tip, wherein the distal portion of the delivery catheter comprises a plurality of segments defined by varying durometers, wherein the plurality of segments of the distal portion comprises at least a second segment extending from and generally planar with the proximal portion, wherein the plurality of segments of the distal portion of the delivery catheter comprises two or more coterminous pre-shaped curved portions that together extend through an arc of about 250 degrees to about 340 degrees when in a resting state prior to use of the delivery catheter for implantation, wherein the two or more coterminous pre-shaped curved portions comprise at least two coterminous curved portions having different curve radii, wherein the distal tip is oriented in a direction towards the proximal portion or the second segment when projected onto a plane containing the proximal portion and the second segment, and further wherein the durometers of the plurality of segments of the distal portion are less than the first durometer of the first segment, and further wherein the durometer of the plurality of segments of the distal portion increases in a direction from the distal tip to the proximal portion.

2. The catheter of claim 1, wherein the delivery catheter comprises at least four segments, wherein the durometer of the plurality of segments increases by at least 5 D from section to section in the direction from the distal tip to the proximal portion.

3. The catheter of claim 2, wherein the at least four segments comprise the first segment, the second segment, a third segment, and a fourth segment, the first segment being at a proximal end, the second segment being distal to the first segment, the third segment being distal to the second segment, and the fourth segment being distal to the third segment.

4. The catheter of claim 3, wherein the first segment possesses a 72 durometer (D), the second segment possesses a 63 D, the third segment possesses a 55 D, and the fourth segment possesses a 35 D.

5. The catheter of claim 4, wherein the second segment being about 2.00 inches long, the third segment being about 3.62 inches long, and the fourth segment being about 0.1 inches long.

6. The catheter of claim 2, wherein the delivery catheter comprises at least five segments.

7. The catheter of claim 2, wherein the delivery catheter comprises at least six segments.

8. The catheter of claim 2, wherein the delivery catheter comprises at least seven segments.

9. The catheter of claim 2, wherein, the delivery catheter comprises at least eight segments.

10. The catheter of claim 1, wherein the two or more coterminous pre-shaped curved portions that together extend through an arc of about 250 degrees to about 340 degrees comprise at least a first curved portion distal to the first segment of the delivery catheter and a second curved portion distal to the first curved portion, wherein the first curved portion extends through an arc of about 135 degrees to about 250 degrees and the second curved portion extends through an arc of about 100 degrees to about 160 degrees.

11. The catheter of claim 10, wherein the first curved portion extends through an arc of about 165 degrees to about 205 degrees and the second curved portion extends through an arc of about 120 degrees to about 140 degrees.

12. The catheter of claim 10, wherein the two or more coterminous pre-shaped curved portions together extend through an arc of about 250 degrees to about 310 degrees.

13. The catheter of claim 1, wherein the two or more coterminous pre-shaped curved portions that together extend through an arc of about 250 degrees to about 340 degrees comprise:
a first curved portion distal to the first segment of the delivery catheter comprising a curve radius between about 30 millimeters and about 50 millimeters and a length of about 120 millimeters to about 130 millimeters; and
a second curved portion comprising a curve radius between about 8 millimeters and about 10 millimeters and a length of about 18 millimeters to about 22 millimeters.

14. A delivery catheter for implanting an electrical lead to a right atrium of a heart in close proximity to a His bundle, the delivery catheter defining a lumen through which an electrical lead can be advanced, such that the electrical lead can extend distally from a distal tip terminating the delivery catheter when being implanted, the delivery catheter further comprising:

a proximal portion comprising a first segment of the delivery catheter, wherein the first segment possesses a first durometer (D); and a distal portion of the delivery catheter being hook-shaped and terminating in the distal tip, wherein the distal portion of the delivery catheter comprises a plurality of pre-shaped segments when in a resting state and prior to use of the delivery catheter for implantation defined by varying durometers, wherein the plurality of pre-shaped segments of the distal portion comprises at least a second segment extending from and generally planar with the proximal portion, wherein the delivery catheter comprises at least four segments, wherein the at least four segments comprise the first segment the second segment, a third segment, and a fourth segment, the third segment being distal to the second segment, and the fourth segment being distal to the third segment, wherein the durometers of the plurality of pre-shaped segments of the distal portion are less than the first durometer of the first segment, and further wherein the durometer of the plurality of pre-shaped segments of the distal portion increases in a direction from the distal tip to the proximal portion, wherein the plurality of pre-shaped segments of the distal portion of the delivery catheter comprises two or more pre-shaped curved portions that together extend through an arc of about 180 degrees to about 250 degrees, wherein the two or more pre-shaped curved portions comprise at least a first curved portion distal to the first segment of the delivery catheter and a second curved portion distal to the first curved portion with a linear disposed therebetween, wherein the first curved portion extends through an arc of about 75 degrees to about 115 degrees and the second curved portion extends through an arc of about 100 degrees to about 160 degrees, and further wherein the distal tip is oriented in a direction towards the proximal portion or the second segment when projected onto a plane containing the proximal portion and the second segment.

15. The catheter of claim 14, wherein the first segment possesses a 72 D, the second segment possesses a 63 D, the third segment possesses a 55 D, and the fourth segment possesses 35 D.

16. The catheter of claim 14, wherein the two or more curved portions have different curve radii.

17. The catheter of claim 14, wherein the first curved portion extends through an arc of about 85 degree to about 100 degrees and the second curved portion extends through an arc of about 120 degrees to about 140 degrees.

18. The catheter of claim 14, wherein the two or more pre-shaped curved portions together extend through an arc of about 200 degrees to about 240 degrees.

19. The catheter of claim 14, wherein the first curved portion distal to the first segment of the delivery catheter comprises a curve radius between about 35 millimeters and about 45 millimeters and a length of at out 60 millimeters to about 70 millimeters wherein the second curved portion comprises a curve radius between about 8 millimeters and about 10 millimeters and a length of about 18 millimeters to about 22 millimeters, and further wherein the linear portion has a length of about 50 millimeters to about 60 millimeters.

20. A catheter for implanting an electrical lead to a right atrium of a heart in close proximity to a His bundle, the catheter comprising:

a proximal portion; and a distal portion being generally planar and hook-shaped, and terminating in a distal tip, wherein the catheter comprises a plurality of pre-shaped segments when in a resting state and prior to use of the delivery catheter for implantation defined by varying durometers, wherein the plurality of pre-shaped segments include four segments, wherein the four segments comprise a first segment, a second segment, a third segment, and a fourth segment, wherein the first segment is at a proximal end, the second segment being distal to the first segment, the third segment being distal to the second segment, and the fourth segment being distal to the third segment, and further wherein the first segment possesses a 72 durometer (D), the second segment possesses a 63 D the third segment possesses a 55 D, and the fourth segment possesses a 35 D.

21. The catheter of claim 20, wherein the second segment is about 2.00 inches long, the third segment is about 3.62 inches long, and the fourth segment is about 0.1 inches long.

22. A catheter for implanting an electrical lead to a right atrium of a heart in close proximity to a His bundle, the catheter comprising:

a proximal portion; and a distal portion being generally planar and hook-shaped, and terminating in a distal tip, wherein the catheter comprises a plurality of pre-shaped segments when in a resting state and prior to use of the delivery catheter for implantation that comprises four segments, the four segments comprise a first segment, a second segment, a third segment, and a fourth segment, wherein the first segment is at a proximal end, the second segment being distal to the first segment, the third segment being distal to the second segment, and the fourth segment being distal to the third segment, and further wherein the first segment possesses a 72 D, the second segment possesses a 63 D, the third segment possesses a 55 D, and the fourth segment possesses a 35 D.

* * * * *

UNITED STATES PATENT AND TRADEMARK OFFICE
CERTIFICATE OF CORRECTION

PATENT NO. : 7,647,124 B2  Page 1 of 1
APPLICATION NO. : 11/741576
DATED : January 12, 2010
INVENTOR(S) : Terrell M. Williams

It is certified that error appears in the above-identified patent and that said Letters Patent is hereby corrected as shown below:

Column 11
Line 31, delete "linear disposed" and insert in place thereof -- ...linear portion disposed... -- therefor.
Line 47, delete "degree" and insert in place thereof -- ...degrees... -- therefor;

Column 12
Line 4, delete "at out" and insert in place thereof -- ...about... -- therefor.

Signed and Sealed this

Twenty-seventh Day of April, 2010

David J. Kappos
*Director of the United States Patent and Trademark Office*